(12) United States Patent
Frankel et al.

(10) Patent No.: US 7,699,852 B2
(45) Date of Patent: Apr. 20, 2010

(54) FENESTRATED BONE TAP AND METHOD

(75) Inventors: Bruce M. Frankel, Memphis, TN (US); Scott D. Koysh, Lago Vista, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 14 days.

(21) Appl. No.: 10/717,379

(22) Filed: Nov. 19, 2003

(65) Prior Publication Data

US 2005/0107800 A1    May 19, 2005

(51) Int. Cl.
    A61B 17/58    (2006.01)
    A61F 5/04     (2006.01)

(52) U.S. Cl. ...................................................... 606/92

(58) Field of Classification Search ............... 606/62, 606/72, 73, 92, 93, 94, 99, 104
    See application file for complete search history.

(56) References Cited

U.S. PATENT DOCUMENTS

| | | | | |
|---|---|---|---|---|
| 4,537,185 A | * | 8/1985 | Stednitz | 606/73 |
| 4,653,338 A | * | 3/1987 | Yeomans | 74/318 |
| 4,653,489 A | | 3/1987 | Tronzo | |
| 4,903,691 A | * | 2/1990 | Heinl | 606/70 |
| 5,047,030 A | | 9/1991 | Draenert | |
| 5,456,267 A | | 10/1995 | Stark | |
| 5,499,986 A | * | 3/1996 | Dimarco | 606/104 |
| 5,514,137 A | * | 5/1996 | Coutts | 606/62 |
| 5,601,559 A | | 2/1997 | Melker et al. | |
| 5,725,581 A | | 3/1998 | Branemark | |
| 5,733,307 A | | 3/1998 | Dinsdale | |
| 5,902,231 A | * | 5/1999 | Foley et al. | 600/114 |
| 6,048,343 A | * | 4/2000 | Mathis et al. | 606/72 |
| 6,096,042 A | * | 8/2000 | Herbert | 606/80 |
| 6,159,179 A | * | 12/2000 | Simonson | 604/117 |
| 6,210,376 B1 | | 4/2001 | Grayson | |

(Continued)

FOREIGN PATENT DOCUMENTS

CA    2546578 A1    6/2005

(Continued)

OTHER PUBLICATIONS

Chappius, et al, "Fixation Strength Studies with Fenestrated Cemented Pedicle Screws in Human Cadaver", (2 pgs).

(Continued)

Primary Examiner—Anu Ramana
(74) Attorney, Agent, or Firm—Sprinkle IP Law Group

(57) ABSTRACT

A bone tap may be used to deliver fluid into bone to stabilize and/or strengthen the bone. The bone tap may include a passage. A distal portion of the bone tap may be threaded. In some embodiments, openings in a distal portion of the bone tap may communicate with the passage. The bone tap may be driven into bone, and material may be introduced to the passage. Material introduced to the passage may enter the bone through the openings. Thread flights of the bone tap proximal to the openings may inhibit retrograde backflow of material during introduction of the material into the bone. Material deposited in the bone may strengthen a bone and/or augment fixation of a bone fastener in the bone.

17 Claims, 11 Drawing Sheets

U.S. PATENT DOCUMENTS

| | | | |
|---|---|---|---|
| 6,214,012 | B1 | 4/2001 | Karpman et al. |
| 6,217,581 | B1 * | 4/2001 | Tolson .......................... 606/86 |
| 6,402,758 | B1 | 6/2002 | Tolson |
| 6,565,572 | B2 | 5/2003 | Chappius |
| 6,610,079 | B1 * | 8/2003 | Li et al. ....................... 606/232 |
| 6,622,731 | B2 * | 9/2003 | Daniel et al. ................. 128/898 |
| 6,679,890 | B2 * | 1/2004 | Margulies et al. ............. 606/94 |
| 6,752,809 | B2 * | 6/2004 | Gorek .......................... 606/92 |
| 6,755,835 | B2 * | 6/2004 | Schultheiss et al. ........... 606/73 |
| 2007/0276402 | A1 | 11/2007 | Frankel et al. |

FOREIGN PATENT DOCUMENTS

| | | |
|---|---|---|
| EP | 0557899 A1 * | 1/1993 |
| FR | 2820630 | 8/2002 |
| WO | WO8806023 | 8/1988 |
| WO | WO 2005051208 A1 | 6/2005 |

OTHER PUBLICATIONS

Cook, et al, "Biomechanical Evaluation and Preliminary Clinical Experience with an Expansive Pedicle Screw Design", *Journal of Spinal Disorders*, 13(3):230-236.

Frankel, B., "Segmental polymethylmethacrylate-augmented pedicle screw fixation for reconstruction of unstable osteoporotic burse fractures", *submitted to JNS: Spine* Jan. 2003.

Introducing a New Solution to the Challenge of Securing Maximum Bone Purcahse: The Innovative Omega21 Expandable Screw for Spine Fixation, *EBI Spine Systems*, 2002 (2 pgs).

Mecron, Berlin, XP002319550, "B. Osteosynthese Osteosynthesis Internal Fixation, " p. B33 (1980).

International Preliminary Report on Patentability and Written Opinion issued in PCT/US2004/036895 mailed May 22, 2006, 8 pages.

Department of Health and Human Services, Section 510(k) for K052638, mailed Nov. 7, 2005, 3 pages.

International Search Report, International Searching Authority, European Patent Office, International Application No. PCT/US2004/036895, mailed Mar. 14, 2005, 4 pgs.

Examination Report, European Patent Office, European Patent Application No. EP04800786, mailed Apr. 8, 2009, 2 pgs.

* cited by examiner

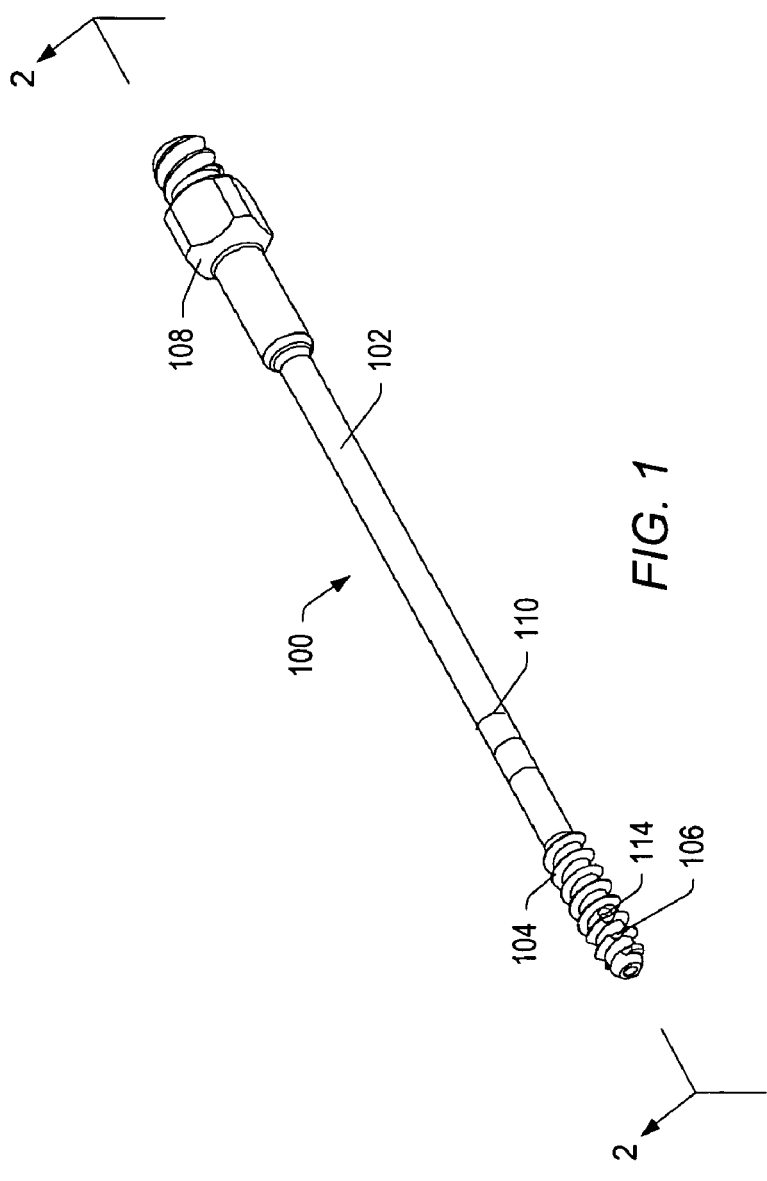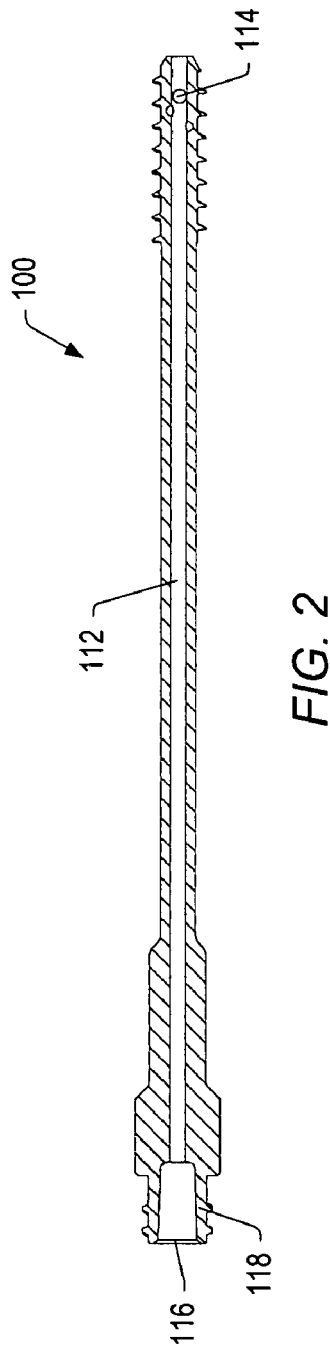

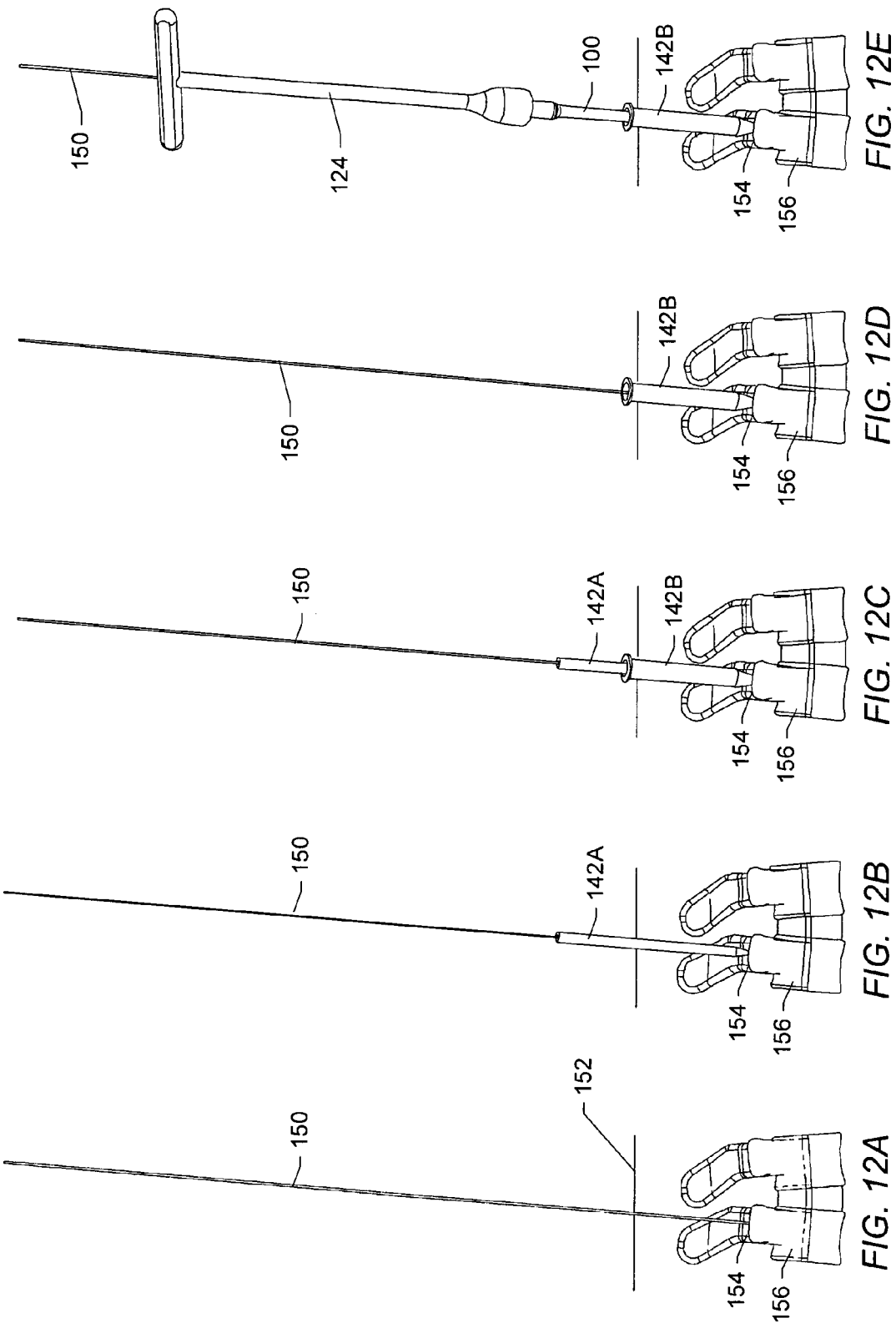

FENESTRATED BONE TAP AND METHOD

BACKGROUND

1. Field of the Invention

The present invention generally relates to apparatus and methods for treatment of human bone. Embodiments of the invention relate to spinal stabilization systems and methods that may be used to treat damaged or diseased bone. Embodiments of the invention relate to systems and methods used to augment fixation of bone fasteners. Embodiments of the invention relate to systems and methods used in vertebroplasty.

2. Description of Related Art

Bone may be treated for damage or degeneration arising from a variety of causes, such as trauma, disease, and/or aging. For example, stabilization of a spine may involve implantation of a system to provide fixation of a portion of the spinal column. As another example, treatment of diseased bone tissue (e.g., a bone tumor) may involve removal of the tumor followed by stabilization procedures to strengthen and/or support remaining bone.

Weakened or softened bone may be difficult to treat with conventional stabilization techniques. For example, spinal stabilization procedures may fail in osteoporotic vertebrae. Osteoporosis (i.e., a bone condition characterized by reduction in bone mass and increased susceptibility to fracture after minimal trauma) may cause loosening and/or pullout of bone fasteners, possibly leading to failure of the spinal stabilization system. Pullout strength may be increased by introducing bone cement (e.g., polymethylmethacrylate) into bone proximate a bone fastener. U.S. Pat. No. 6,565,572 to Chappius, which is incorporated by reference as if fully set forth herein, describes a fenestrated surgical screw. The design allows material to be delivered through a passage in a body of the screw into a skeletal member. Holes in the shank of the screw communicate with the passage and allow injected bone cement to pass into bone surrounding the screw. After curing, the bone cement fixes the screw in place in the bone. A fenestrated bone screw that has been cured in place may be difficult to remove should a subsequent procedure be necessary due to infection, further injury, and/or other causes.

Treatment for fractured or diseased bone may include minimally invasive procedures such as vertebroplasty. In a vertebroplasty procedure, bone cement may be injected into a vertebra to stabilize a fracture and relieve pain associated with the fracture. Other treatments may include steps to restore a natural height of a fractured vertebra followed by injection of bone cement or other material into a cavity in the vertebra. For example, a surgeon may use an inflatable balloon to compact bone, then inject a biomaterial into a cavity. Such balloon procedures have been referred to as "kyphoplasty," and equipment for such procedures may be available from Kyphon, Inc.

One method for introducing bone cement into a vertebra is through a biopsy needle (e.g., a Jamshidi® needle) inserted in an opening in the bone. Limitations of such methods of cement introduction may include retrograde flowback of bone cement along the needle and limited vertebral body fill. Local complications from bone cement leakage (i.e., retrograde flowback) may include radiculopathy and cord compression. Systemic complications from bone cement leakage may include fever, infection, pulmonary embolism, fat embolism, hypoxia, hypotension, myocardial infarction, and sudden death.

SUMMARY

In an embodiment, a bone tap may be used to form a threaded hole of a desired depth in a bone. The bone tap may include a passage and fenestrations for introducing fluid into bone surrounding the tap. The fenestrations may be openings through thread of the bone tap to the passage. Thread flights of a tap portion may inhibit retrograde backflow of fluid during introduction of the fluid into the bone. The fluid may be bone cement. The bone cement may augment fixation of a bone fastener installed in the threaded hole following removal of the bone tap. The bone fastener may be part of a spinal stabilization system.

In some embodiments, a fenestrated bone tap may be used to introduce bone cement into a portion of damaged or diseased bone to stabilize and/or strengthen the bone. The fenestrated bone tap may stabilize or strengthen a vertebra, a sacrum, a femur, a tibia, a radius, and/or a humerus. The fenestrated bone tap may be used to stabilize other types of bone. In some embodiments, a fenestrated bone tap may be used to introduce material into bone tissue in addition to or in lieu of bone cement. In some embodiments, a fenestrated bone tap may be used to introduce medicine (e.g., antibacterial agents), synthetic bone material, bone growth proteins and/or other substances into bone. In some embodiments, one or more bones adjacent to a target bone may be augmented before, during, or after augmentation of the target bone.

In some embodiments, a fenestrated bone tap may be introduced into a patient using minimally invasive procedures. In an embodiment, a set of dilators may be used to create space for and guide the fenestrated bone tap to a target bone. A guide wire may be used to position the dilators and the bone tap.

BRIEF DESCRIPTION OF THE DRAWINGS

Advantages of the present invention will become apparent to those skilled in the art with the benefit of the following detailed description and upon reference to the accompanying drawings in which:

FIG. 1 depicts a perspective view of an embodiment of a bone tap.

FIG. 2 depicts a cross-sectional view of the bone tap taken substantially along plane 2-2 of FIG. 1.

FIGS. 12A-12E depict steps to prepare a vertebral body for tapping.

Figure 3A:
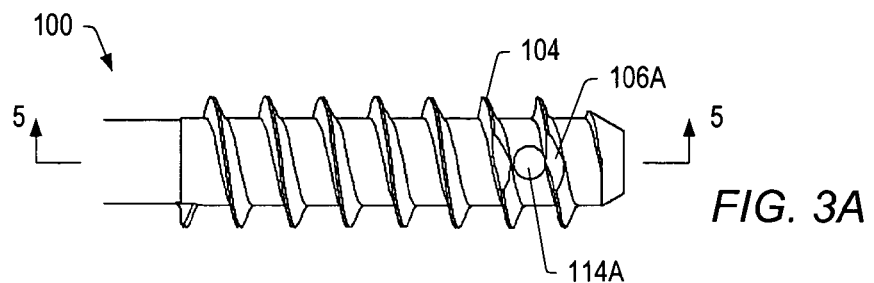
FIGS. 3A-3C depict fenestrations in a distal portion of a bone tap.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

A bone tap may be used to form a threaded opening of a desired depth in a bone. In an embodiment, a bone tap may be used to prepare an opening in a bone for insertion of a bone fastener (e.g., a bone screw) to be used as part of a spinal stabilization system. In some embodiments, a bone tap may include a passage and fenestrations for introducing bone cement into bone proximate a distal portion of the tap. The bone cement may augment fixation of a bone fastener. Bone cement augmentation may increase axial pullout strength and transverse bending stiffness of a bone/fastener interface in a spinal stabilization system. In certain embodiments, a tap may be used to introduce bone cement into a portion of weakened, damaged or diseased bone (e.g., a vertebra) to stabilize and/or strengthen the bone.

FIG. 1 depicts an embodiment of bone tap 100. Bone tap 100 may be made of materials, including, but not limited to, stainless steel, titanium, and/or plastic. Bone tap 100 may include shaft 102. A distal end of bone tap 100 may include threading 104. Threading 104 may include flutes 106. In some embodiments, flutes 106 may be located substantially parallel to a longitudinal axis of shaft 102. In some embodiments, flutes may be angled relative to a longitudinal axis of the shaft. Flutes 106 may allow for removal or control of loose bone material resulting from a tapping procedure. In some embodiments, flutes 106 may extend along a portion (e.g., a distal portion) of threading 104. In certain embodiments, flutes 106 may extend the full length of threading 104.

Bone tap 100 may include tool portion 108. Tool portion 108 may complement a portion of a tool (e.g., a driver) used to facilitate insertion of bone tap 100 into bone. Tool portion 108 may include threading, a square configuration, a hex configuration, and/or other configurations for engaging a tool.

In certain embodiments, bone tap 100 may include indicia 110. Indicia 110 may include a numeric scale. Indicia 110 may allow a user to monitor an insertion depth of bone tap 100 into bone. Monitoring an insertion depth of indicia 110 may allow a user to select a bone screw of an appropriate length to be inserted in the tapped bone.

FIG. 2 depicts a cross-sectional view of an embodiment of a bone tap 100. Bone tap 100 may include passage 112. In an embodiment, passage 112 may be about 0.066 inches in diameter. In some embodiments, the passage may have a non-circular cross section. In some embodiments, bone tap 100 may be cannulated (i.e., passage 112 may extend the full length of the bone tap). A guide wire inserted through the proximal end of passage 112 of bone tap 100 may be used to position the distal end of the bone tap at a target location. In some embodiments, a passage in a bone tap may not extend completely through the bone tap. The passage may terminate prior to a distal end of the bone tap. Terminating the passage prior to the distal end of the passage may limit fluid exiting the bone tap to fluid exiting fenestrations in a wall of the bone tap.

Bone tap 100 may include fenestrations 114 that communicate with passage 112. Fenestrations 114 may have a shape including, but not limited to, circular, oval, or rectangular. Fenestrations 114 may be the same size or different sizes. Sizes of fenestrations 114 may be chosen based on dimensions of the distal end of bone tap 100. Sizes of fenestrations 114 may be chosen to control an amount of fluid that is able to flow from various portions of the tap. In some embodiments, fenestrations 114 may be about 0.060 inches in diameter.

In some embodiments, fluid may be introduced to passage 112 through inlet 116. In certain embodiments, the fluid may be introduced under pressure at inlet 116. The fluid may flow through passage 112 and out fenestrations 114 to a target site. Fluid delivered through bone tap 100 may include, but is not limited to, a gas, a liquid, an emulsion, or a suspension. For example, the fluid may be medical adhesive, bone cement (e.g., polymethylmethacrylate), epoxy, bone healing substance, bone growth promotion substance (e.g., hydroxyapatite or bone morphogenic proteins), radio-opaque dye, medicine (e.g., antibacterial agents), or a combination thereof.

In some embodiments, the proximal end of bone tap 100 may include port 118. Port 118 may facilitate coupling bone tap 100 with a fluid delivery system. In some embodiments, the fluid delivery system may be a syringe, or a metering pump system. Port 118 may include, but is not limited to, threading, a compression fitting, a pipe fitting, or a quick disconnect. In certain embodiments, port 118 may include threading for a standard ASTM (American Society for Testing and Materials) luer lock fitting, or an ISO (International Organization for Standardization) fitting (e.g., ISO 594-1 and 594-2 (double lead)). Threading may form a seal with the fluid delivery system.

Figure 3B:
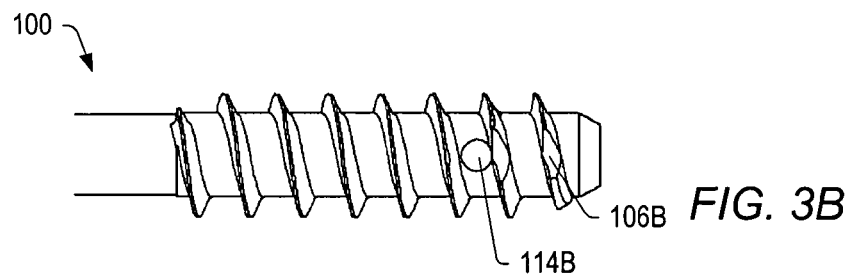
Figure 3C:
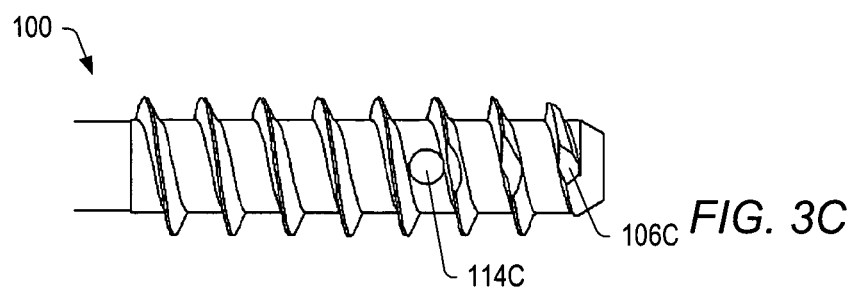

FIGS. 3A-3C depict views of a distal portion of bone tap 100. Fenestrations 114 (e.g., fenestrations 114A, 114B, 114C) may be located between flights of threading 104 of bone tap 100. As shown in FIG. 1, flute 106 may be aligned with fenestration 114. As depicted in FIG. 3A, flute 106A that is aligned with fenestration 114A may extend from the distal end of bone tap 100 beyond the fenestration. As depicted in FIGS. 3B and 3C, flute 106B, 106C aligned with fenestrations 114B, 114C, respectively, may extend between the distal end of bone tap 100 and the fenestrations. In some embodiments, the flutes may be formed at an angle relative to a longitudinal axis of the bone tap. Flutes 106 (e.g., flutes 106A, 106B, 106C) may be sized and/or shaped to promote spreading of material exiting bone tap 100 through fenestrations 114 (e.g., fenestrations 114A, 114B, 114C) in a region of bone surrounding a distal portion of the bone tap. In some embodiments, threading 104 proximal to fenestrations (e.g., fenestrations 114B, 114C) may inhibit spreading of material from the fenestrations toward the proximal end of bone tap 100.

Figure 4:
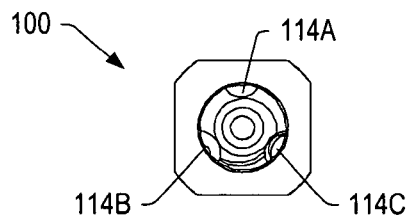
FIG. 4 depicts a distal end view of an embodiment of a bone tap.

Fenestrations 114 may be spaced from each other at selected angular or axial intervals. FIGS. 3A-3C depict fenestrations 114A, 114B, 114C spaced at about 120° intervals between flights of threading 104 of bone tap 100. FIG. 4 depicts an end view of bone tap 100 shown in FIGS. 3A-3C, with fenestrations 114A, 114B, 114C substantially equally spaced around a circumference of a distal portion of bone tap 100. Fenestrations 114 may be confined to a distal portion of bone tap 100 to stop or inhibit backflow of injected material toward the proximal end of the bone tap. In some embodiments, the fenestrations may be formed perpendicular or substantially perpendicular (e.g., within plus or minus 5° of perpendicular) to a longitudinal axis of the bone tap. In some embodiments, one or more of the fenestrations may be angled relative to the longitudinal axis of the bone tap to promote flow of fluid from the bone tap in a desired direction. Fenestrations may be angled relative to the longitudinal axis of the bone tap in a range from about 175° to about 5°.

Figure 5:
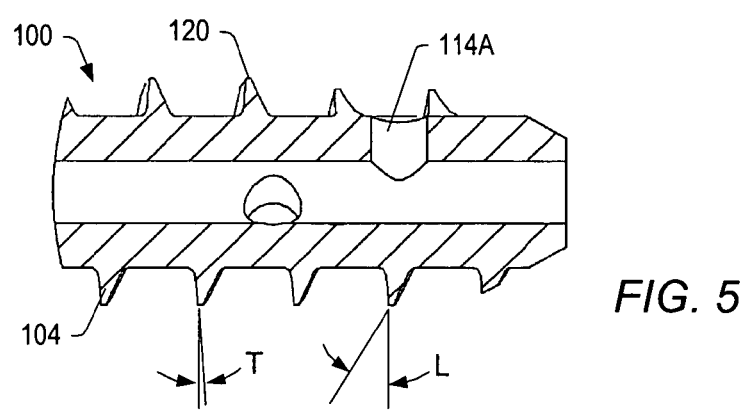
FIG. 5 depicts a cross-sectional view of a distal portion of a bone tap, taken substantially along line 5-5 of FIG. 3A.

FIG. 5 depicts a cross-sectional view of a distal portion of an embodiment of bone tap 100. Threading 104 may have a cross-sectional shape including, but not limited to, rounded, V-shaped, and asymmetrically shaped. Crown 120 of threading 104 may be flat. Threading 104 may have various leading and or trailing angles. For example, a leading angle L may be about 25° and/or a trailing angle T may be about 5°. The pitch of threading 104 may be chosen depending at least upon the size and condition of the bone and the function of the bone fastener to be installed. In an embodiment, a pitch of threading 104 may be about 10 threads per inch.

Figure 6:
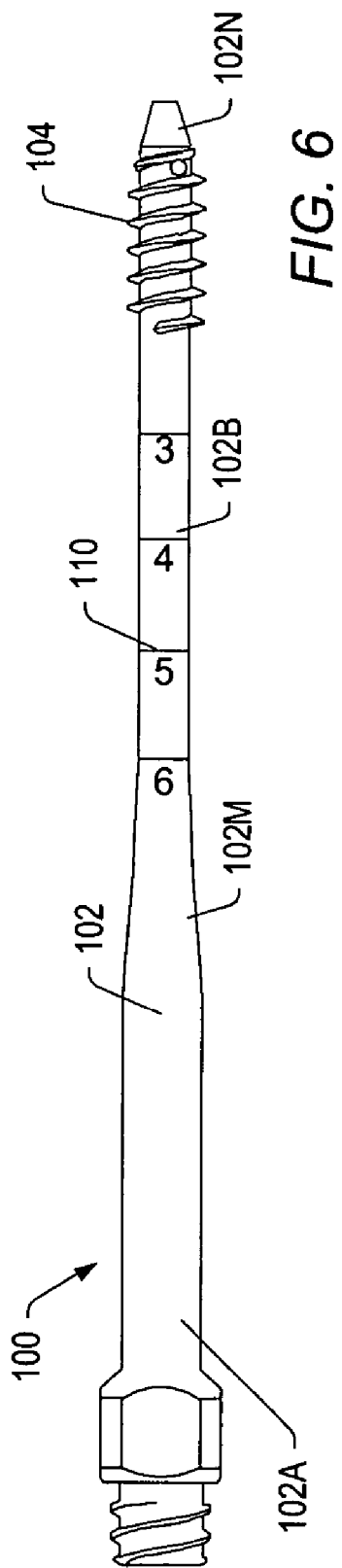
FIG. 6 depicts a front view of an embodiment of a bone tap.

FIG. 6 depicts an embodiment of a bone tap. Bone tap 100 may include tap shaft 102. Tap shaft 102 may include tapered nose section 102N and tapered mid section 102M. Tapered nose section 102N may facilitate starting bone tap 100 in a small hole in a bone. In an embodiment, threading 104 may be unfluted (as shown). In other embodiments, the threading may be fluted. Proximal section 102A of tap shaft 102 may be sized to slide within a cannula of a distractor. Distal section 102B of tap shaft 102 may be of a reduced diameter relative to the major diameter of threading 104 or relative to proximal section 102A. Distal section 102B may include indicia 110. A reduced diameter of distal section 102B may provide annular clearance between bone tap 100 and a distractor used to facilitate placement and use of the bone tap.

A driver may be used to position and insert a bone tap into bone. In some embodiments, a driver may be an integral portion of a bone tap. In certain embodiments, a driver may be removably coupled to a bone tap. A removable driver may be used with bone taps of various sizes. Bone taps used with removable drivers may be disposable.

Figure 7:
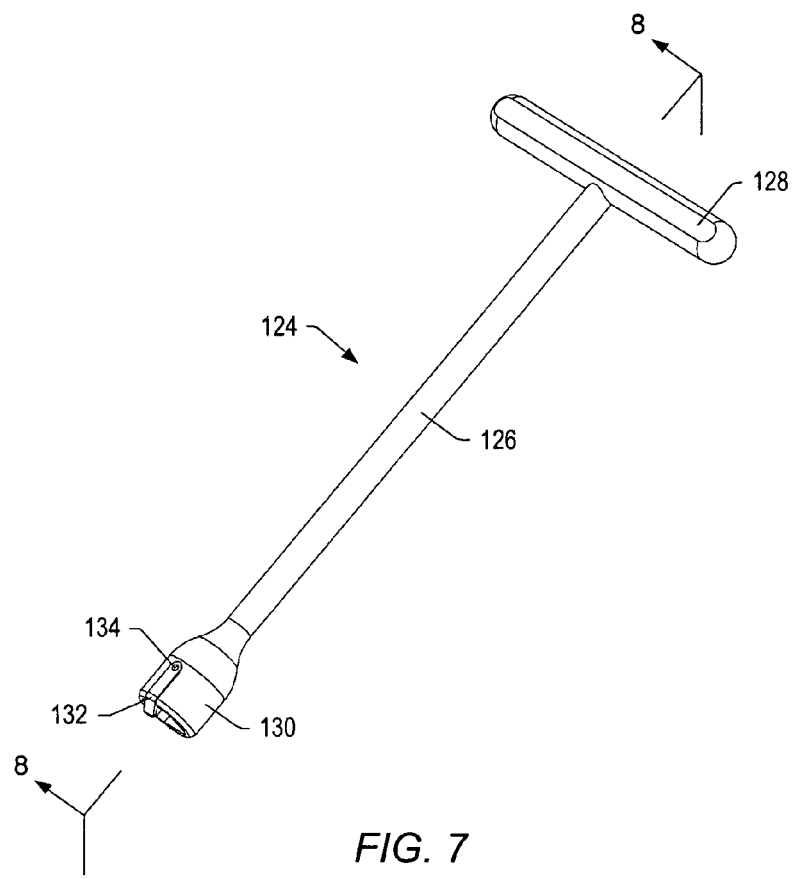
FIG. 7 depicts a perspective view of an embodiment of a driver.

FIG. 7 depicts a perspective view of driver 124 that may be used to drive a bone tap into bone. Driver 124 may include shaft 126 and handle 128. In some embodiments, handle 128 may be a T-shaped handle. Driver 124 may include coupler 130. Coupler 130 may be complementary to a tool portion of a bone tap. Coupler 130 may engage the tool portion of a bone tap by means including, but not limited to, a square socket, a hexagonal socket, or threading. In some embodiments, driver 124 may include a torque indicator. In certain embodiments, driver 124 may be power driven.

In some embodiments, driver 124 may include spring tab 132. Spring tab 132 may be produced from any resilient material, including, but not limited to, stainless steel and plastic. Spring tab 132 may deflect when a threshold force (i.e., assembly force or disassembly force) is applied to driver 124 coupled to a bone tap. During a tapping procedure, spring tab 132 may inhibit separation of driver 124 from a bone tap. Spring tab 132 may be coupled to driver 124 with fastener 134. Fastener 134 may be, but is not limited to, a screw, a weld, a rivet, or a pin. In other embodiments, a bone tap may be coupled to a driver by any of various other arrangements, including, but not limited to, mating threads, a collet, or a threaded collar.

Figure 8:
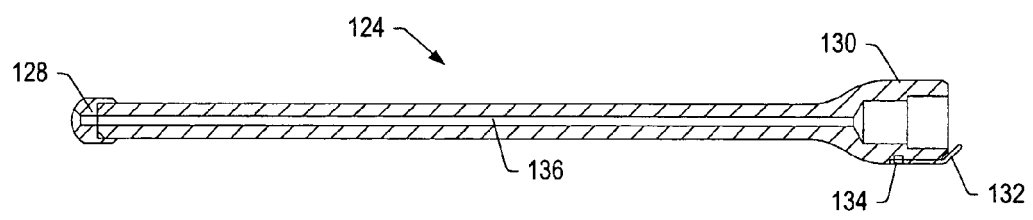
FIG. 8 depicts a cross-sectional view of a driver, taken substantially along plane 8-8 of FIG. 7.

FIG. 8 depicts a cross-sectional view of driver 124. Channel 136 may extend the length of driver 124. Channel 136 of driver 124 may align with a passage in a bone tap coupled to the driver. In some embodiments, a guide wire inserted through an opening in handle 128 may pass through an opening in the distal end of the bone tap. In some embodiments, a guide wire extending through driver 124 and a bone tap coupled to the driver may allow placement of the bone tap at a target site.

Figure 9:
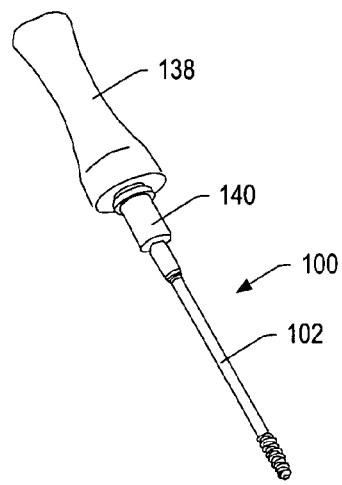
FIG. 9 depicts a perspective view of an embodiment of a bone tap coupled to a handle.

FIG. 9 depicts an embodiment of handle 138 coupled to bone tap 100. A proximal portion of shaft 102 of bone tap 100 may include at least one flat side. An opening in the distal end of handle 138 may complement a cross-sectional shape of the proximal portion of shaft 102, such that the shaft rotates as the handle is rotated. In some embodiments, the proximal portion of shaft 102 may include an indent.

In some embodiments, handle 138 may include a detent mechanism to inhibit separation of bone tap 100 from the handle. In certain embodiments, handle 138 may include spring-loaded release 140. When spring-loaded release 140 is in a resting position, a detent in removable handle 138 may be seated in an indent in a proximal portion of bone tap 100. When spring-loaded release 140 is drawn upwards, the detent may disengage from the indent to allow separation of removable handle 138 and bone tap 100. A fluid delivery system may be coupled to the bone tap when the handle is removed. The fluid delivery system and/or the bone tap may include an o-ring or other system to inhibit fluid leakage.

In certain embodiments, a handle for coupling to a bone tap may include a reservoir and an injection device for injecting material (e.g., bone cement) from the reservoir into bone. The injection device may have a locking mechanism to inhibit release of material from the reservoir during insertion of a bone tap. After insertion of the bone tap into bone, the locking mechanism may be disengaged to allow passage of the material from the reservoir through a distal portion of the bone tap and into the bone.

In an embodiment, a bone tap including a passage and one or more fenestrations may be used in a procedure for installing a spinal stabilization system. Bone cement may be introduced into the passage and forced through the fenestrations to augment fixation of a bone fastener of the spinal stabilization system. In some embodiments, augmentation may be used to increase strength in a bone compromised by osteoporosis. A surgical procedure may include posterior transpedicular, transthoracic, anterolateral or other approaches. In some embodiments, a targeting needle may be used in combination with a fluoroscope to target a selected portion of a vertebra (e.g., a pedicle). In some embodiments, a surgeon may identify a target bone as "soft" by analyzing images and/or by probing the bone.

In some embodiments, one or more dilators may be used to push aside tissue and create space to access vertebral bone. In some embodiments, tissue dilators of increasing diameter may be used to establish sufficient working space to accommodate instruments and spinal stabilization system components. Dilators in an instrumentation set may increase in diameter incrementally by a selected amount. FIGS. 10A-10B and 11A-11B depict selected views of first dilator 142A and second dilator 142B. Dilators 142A, 142B may include bores 144 and tapered nose sections 146. Dilator 142B may include rim 148.

Figure 10A:
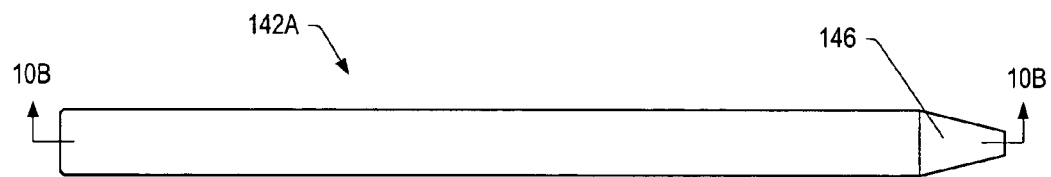
FIG. 10A depicts a front view of an embodiment of a first dilator.
Figure 10B:
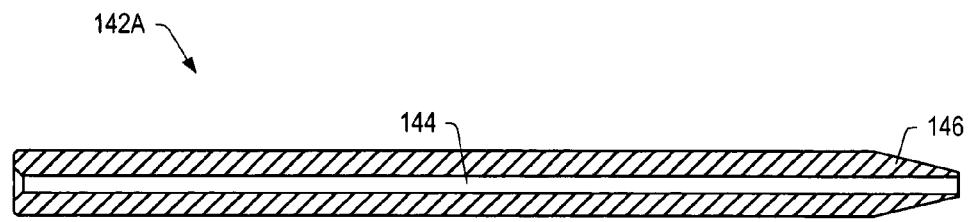
FIG. 10B depicts a cross-sectional view of the embodiment of the first dilator taken substantially along line 10B-10B of FIG. 10A.
Figure 11A:
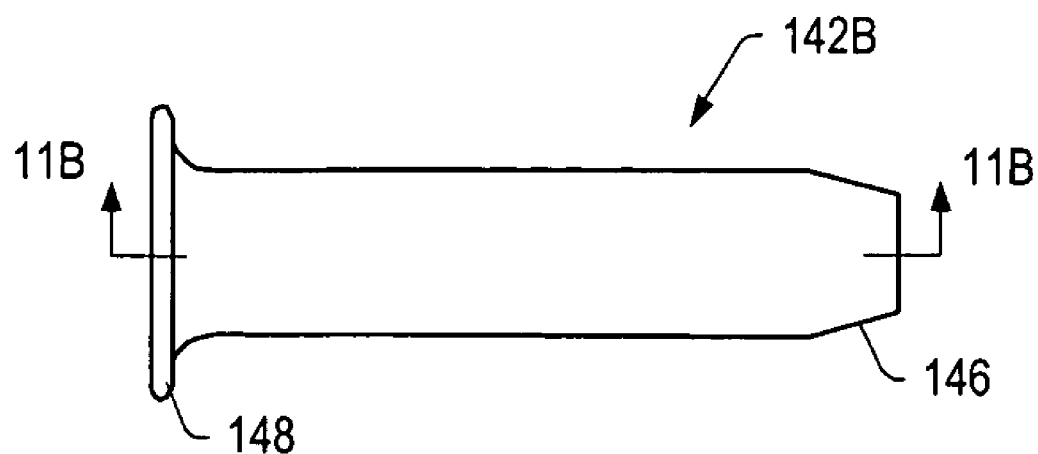
FIG. 11A depicts a front view of an embodiment of a second dilator.
Figure 11B:
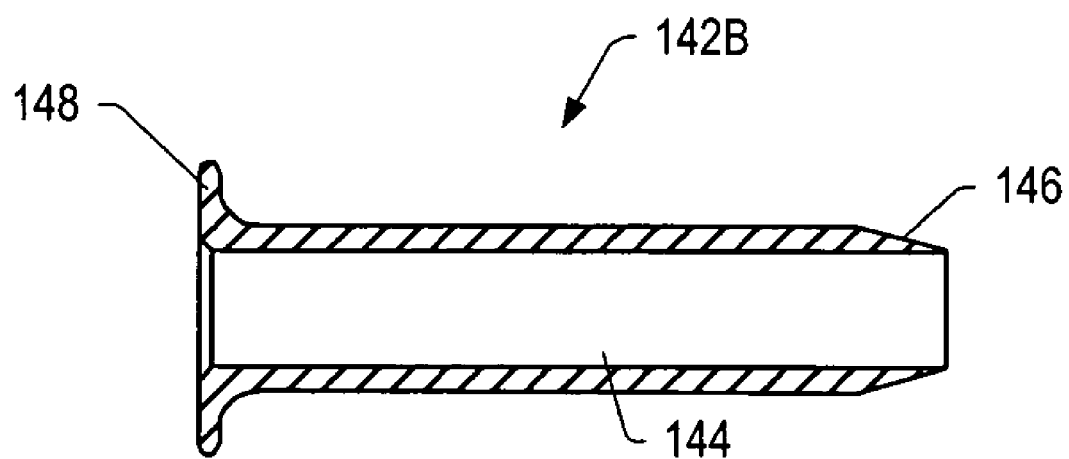
FIG. 11B depicts a cross-sectional view of the embodiment of the second dilator taken substantially along line 11B-11B of FIG. 11A.

Bore 144 of dilator 142A, which is depicted in FIG. 10B, may be sized to receive a guide wire. Bore 144 of dilator 142B, which is depicted in FIG. 11B, may be slightly larger than an outer diameter of dilator 142A. Dilator 142B may slide over dilator 142A during use. In an embodiment, bore 144 of dilator 142B may be slightly larger than the major diameter of threading 104 of bone tap 100. In some embodiments, the bore of the second dilator may be slightly larger than the major diameter of thread of a bone fastener to be positioned though the dilator into bone. During use, the wall of dilator 142B may act as a barrier to the spread of the bone cement from desired areas.

A targeting needle (e.g., a Jamshidi® needle) may be positioned on a surface of a bone that is to be stabilized or repaired. The targeting needle may include an outer shaft with a handle, and an inner pointed member that fits within, and is removable from, the outer shaft. In some embodiments, the inner pointed member may attach to the outer shaft by threading. A top of the inner pointed member may be an impact surface for driving the targeting needle into a patient. The targeting needle may be driven into a patient until the outer shaft is positioned against bone. Position of the targeting needle may be monitored using fluoroscopy.

After a targeting needle is positioned, the inner pointed member may be removed from the outer shaft. A guide wire may be positioned through the outer shaft and into bone. In some embodiments, the guide wire may be K-wire. The guide wire may have any desired length. In some embodiments, the length of the guide wire may be between about 6 inches and about 24 inches in length. In an embodiment, the length of the guide wire may be about 18 inches. A length of the guide wire may be sufficient to allow a portion of the guide wire to be gripped at all times during insertion, removal and use of tools so that the guide wire is not inadvertently advanced or removed during use.

In some embodiments, the end of the guide wire that is to be inserted into bone may have a pointed tip. The pointed tip may facilitate entry of the guide wire into bone. In some embodiments, the end of the guide wire that is to be inserted into bone may have a blunt tip. A blunt tip may inhibit undesired advancement of the guide wire into the bone during use.

In some embodiments, the guide wire may be pushed into bone. In other embodiments, the guide wire may be impacted into the bone. If the guide wire is to be impacted into the bone, a long distractor (such as the distractor depicted in FIG. 10A) may be placed over the guide wire and against the targeting needle to stabilize the guide wire. An impact device may then be used against an end of the guide wire to drive an opposite end of the guide wire into bone. Lateral fluoroscopic images may be obtained to indicate the position of the guide wire. Care should be taken to avoid kinking the guide wire when the guide wire is being inserted into bone. FIG. 12A depicts guide wire 150 positioned through an incision formed in skin 152. Guide wire 150 is inserted into pedicle 154 and vertebral body 156.

Once the guide wire has been passed through the targeting needle and the targeting needle has been removed, the guide wire may be used as a guide to position one or more successively sized dilators at a target location. A dilator may form an opening through soft tissue to the vertebral body. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact the vertebral body. A distal end of a dilator may be tapered to facilitate positioning of the dilator proximate the vertebral body.

FIG. 12B depicts first dilator 142A positioned around guide wire 150. FIG. 12C depicts second dilator 142B positioned around first dilator 142A. Once second dilator 142B is in position, first dilator 142A may be removed. Lengths of dilators in a successively sized set may decrease with increasing diameter to facilitate removal of the smaller dilators. Care should be taken to avoid dislodging guide wire 150 during insertion and removal of the dilators. FIG. 12D depicts second dilator 142B positioned around guide wire 150 following removal of the first dilator.

After tissue dilation has been achieved, guide wire 150 and a large diameter dilator (e.g., second dilator 142B shown in FIG. 12D) may be used to guide a bone tap and/or bone fastener insertion instruments toward a target location. In some embodiments, a bone awl may be used to breach vertebral bone to allow for insertion of the bone tap. In some embodiments, an initial passage may be formed in pedicle 154 and vertebral body 156 using a drill. FIG. 12E depicts bone tap 100 positioned in second dilator 142B. Bone tap 100 may be sized to fit snugly inside second dilator 142B. Bone tap 100 may be coupled to driver 124.

Guide wire 150 may be used to position bone tap 100 at a target location of pedicle 154. The distal end of guide wire 150 may be positioned in pedicle 154 and into vertebral body 156. The proximal end of guide wire 150 may be inserted into an opening at the distal end of bone tap 100. Guide wire may be held near second dilator 142B. Bone tap 100 may be moved down guide wire 150. When the proximal end of guide wire 150 extends beyond the proximal end of driver 124, the guide wire may be held above the driver and released near dilator 142B. Bone tap 100 may be moved down guide wire 150 until the distal end of the bone tap contacts pedicle 154. Before advancing bone tap 100 into pedicle 154, a position of indicia on a shaft of the bone tap may be noted relative to a selected reference point (e.g., the top of the second dilator). Tap may be advanced through pedicle 154 and into vertebral body 156

Figure 13A:
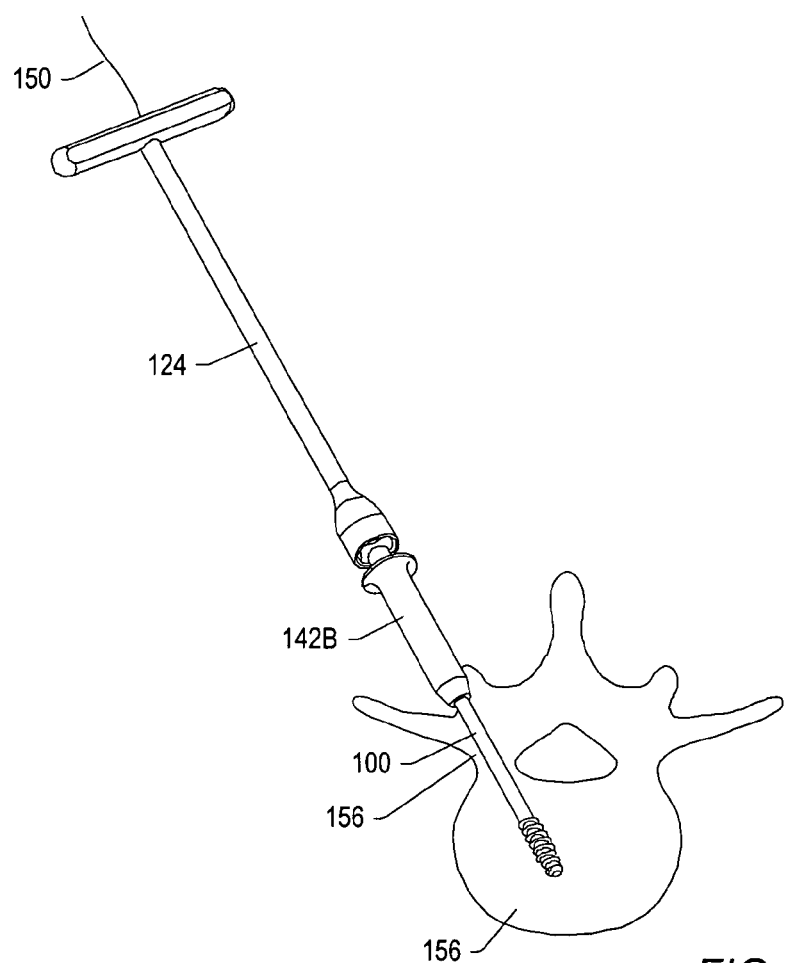
FIGS. 13A-13F depict steps in a procedure to install a bone fastener in a vertebra using a fenestrated bone tap.

FIG. 13A depicts a front view representation of bone tap 100 coupled to driver 124 after insertion of the bone tap through pedicle 154 and into vertebral body 156. In some embodiments, bone tap 100 may be sized to form threading of major diameter slightly smaller than a major diameter of threading of a bone fastener to be inserted into a threaded passage formed by the bone tap. For example, a major diameter of threading of bone tap 100 may be about 0.05 mm to about 0.8 mm less than a major diameter of a bone fastener to be inserted into a threaded passage formed by the bone tap. In some embodiments, a major diameter of threading of bone tap 100 may be about 0.5 mm less than a major diameter of a bone fastener to be inserted into a threaded passage formed by the bone tap. A position of bone tap 100 may be monitored using a fluoroscope. When bone tap 100 has been inserted to a desired depth, advancement of indicia 110 may be noted relative to the selected reference point. Advancement of indicia 110 relative to the selected reference point may be used to determine an appropriate length of a bone fastener to be inserted in the pedicle.

Figure 13B:
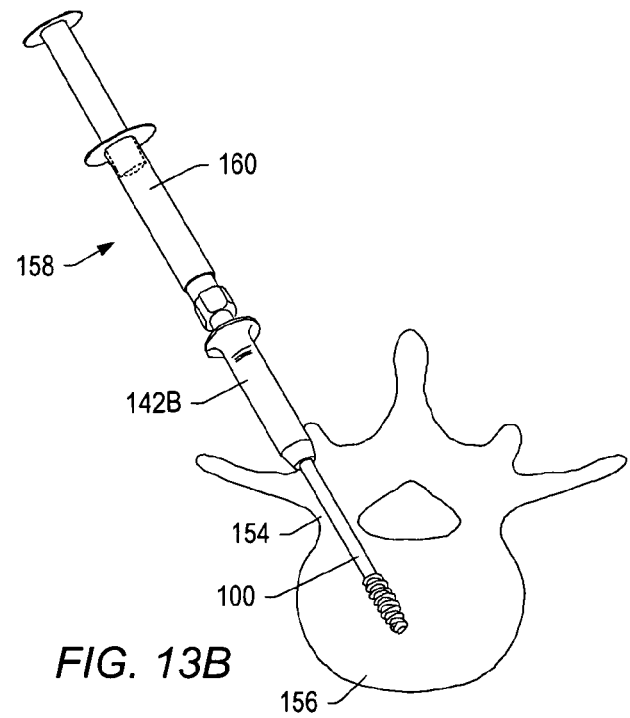
Figure 13C:
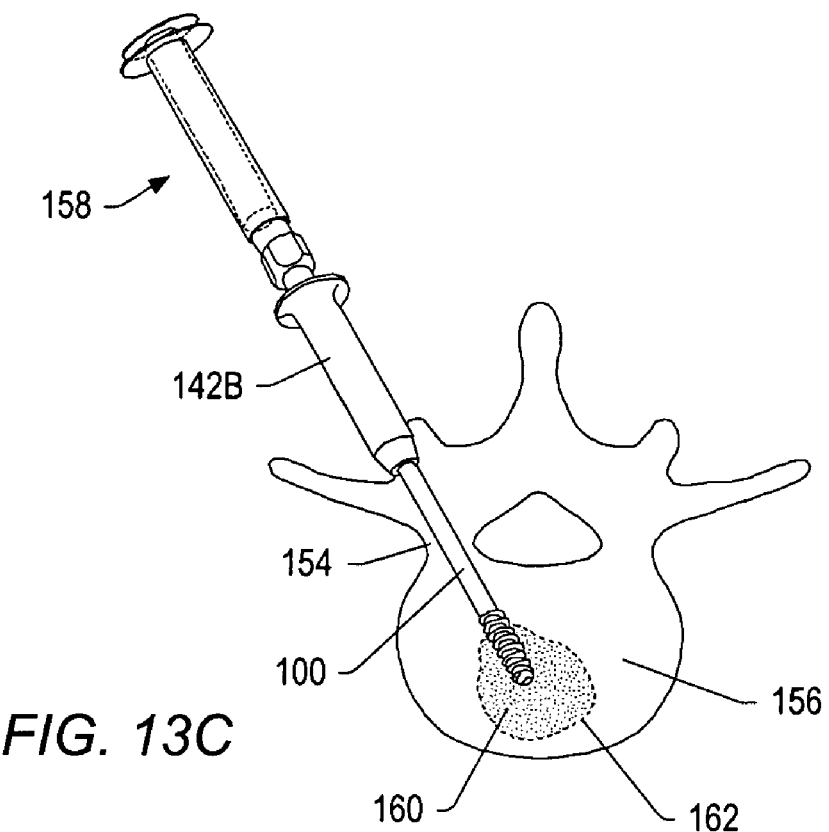

After an opening of a desired length has been tapped in vertebra 156, driver 124 may be removed from bone tap 100. Guide wire 150 may be removed from the patient. An injection device may be coupled to the proximal end of bone tap 100. Bone cement may be placed in the injection device before or after the injection device is coupled to the bone tap. FIG. 13B depicts syringe 158 coupled to bone tap 100. Bone cement 160 or other fluid may be injected from syringe 158 into bone tap 100. FIG. 13C depicts syringe 158 after injection of bone cement 160 into vertebra 156. Bone cement 160 may contain additives including, but not limited to, a bone healing substance, a bone growth promotion substance, and/or a dye to enhance fluoroscopic images of the bone cement.

In some embodiments, other materials may be injected before and/or after injection of bone cement 160.

During injection, bone cement 160 may be in a fluid state. Syringe 158 may force bone cement 160 toward a distal end of bone tap 100, out of fenestrations 114 and/or an opening in the distal end of the bone tap, and into region 162. Fenestrations 114 and flutes (if present) may allow bone cement to spread at least partially throughout region 162. Threading 104 proximal to fenestrations 114 may inhibit bone cement from migrating to areas outside the vertebra. Keeping bone cement 160 in a desired region may reduce a quantity of bone cement required to perform a procedure and/or reduce a risk of complications. A location of injected bone cement 160 may be monitored fluoroscopically.

After injection of bone cement 160 in region 162, bone tap 100 may be left in the bone for a chosen amount of time to allow the bone cement to begin to cure. In some embodiments, additional bone cement may be injected after bone tap 100 is partially withdrawn from the bone. Withdrawing the bone tap 100 and injecting additional cement one or more times may allow more complete filling of region 162 with bone cement 160. In certain embodiments, bone cement 160 may be allowed to harden at least partially before bone tap 100 is completely withdrawn from the bone, such that the cement-filled bone in region 162 maintains a shape complementary to a distal portion of bone tap 100 following withdrawal of the bone tap. Bone tap 100 may be removed before bone cement 160 hardens completely. In some embodiments, bone cement 160 in region 162 may have a plastic or putty-like consistency when bone tap 100 is removed. In certain embodiments, bone tap 100 may be left in vertebra 156 for about 5, 20, or 55 minutes after injection of bone cement 160. After the desired time has passed, bone tap 100 may be removed by rotating the tap until threading 104 is disengaged from vertebra 156.

Figure 13D:
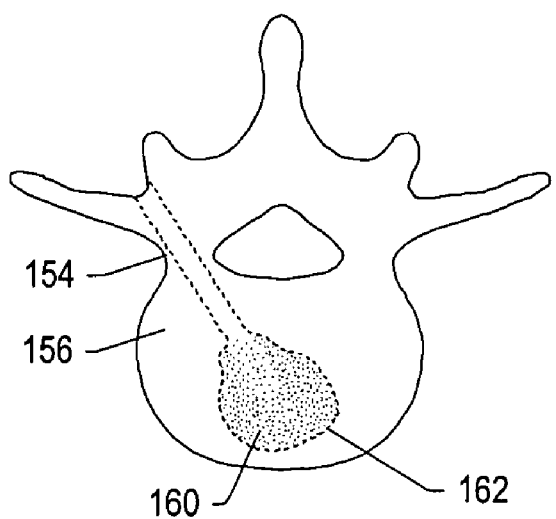

In some embodiments, a syringe used to introduce fluid through the bone tap may be removed from the bone tap. A driver may be coupled to the bone tap to facilitate removal of the bone tap from the vertebral body and pedicle. FIG. 13D depicts a representation of a tapped opening formed after injection of bone cement using a fenestrated bone tap.

Bone cement may be difficult to remove from a passage through the bone tap and/or from fenestrations in the bone tap. In some embodiments, bone tap 100 may be disposable. In certain embodiments, driver 124 may be reusable.

After removal of a bone tap from a vertebra, bone cement in the vertebra may be allowed additional time to cure. A bone fastener of an appropriate length may be selected for insertion in vertebra. With bone cement 160 already in place, a surgeon may be able to choose from any of a variety of standard (e.g., non-fenestrated) bone fasteners. In some embodiments, a bone fastener may include a polyaxial collar. In certain embodiments, a sleeve may be used to guide installation of a bone fastener in a vertebra. Instruments may be inserted into the sleeve to manipulate the bone fastener.

Figure 13E:
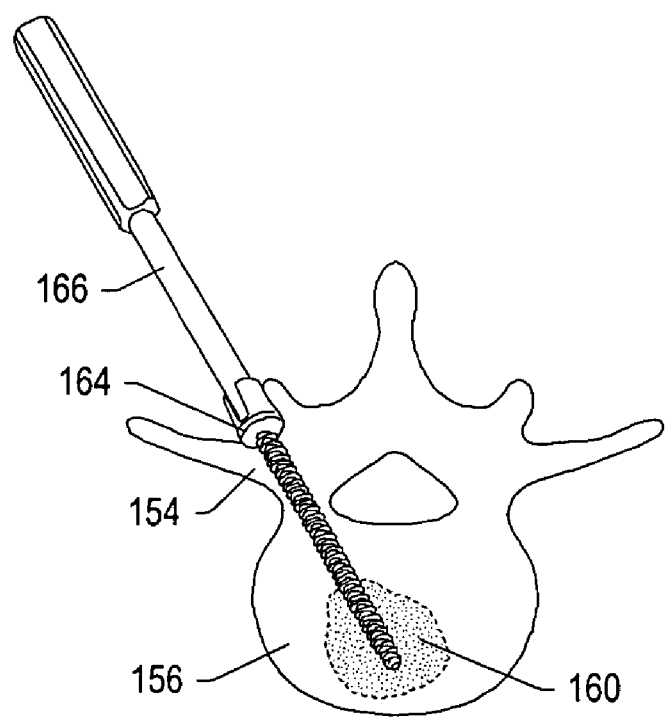
Figure 13F:
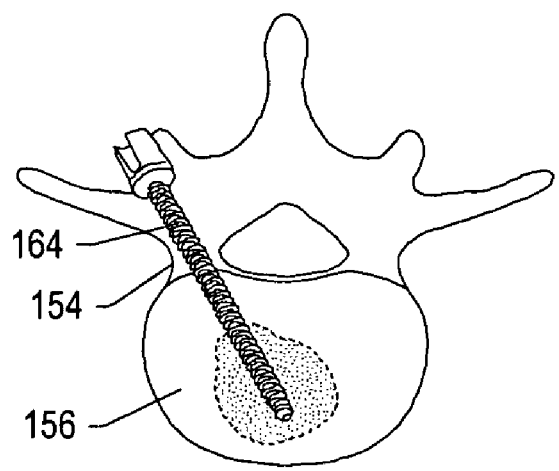

When bone cement 160 has reached a desired hardness, an inserter may be used to insert a bone fastener in vertebral body 156. FIG. 13E depicts bone fastener 164 that has been installed in vertebral body 156 with inserter 166. Bone fastener 164 may be advanced into pedicle 154 under fluoroscopic guidance to inhibit breaching of the pedicle walls. In some embodiments, a hole may be tapped and/or a fastener length may be chosen to achieve uni-cortical purchase. In other embodiments, a hole may be tapped and/or a fastener length may be chosen to achieve bi-cortical purchase. FIG. 13F depicts bone fastener 164 installed in pedicle 154 after removal of the inserter.

Figure 14A:
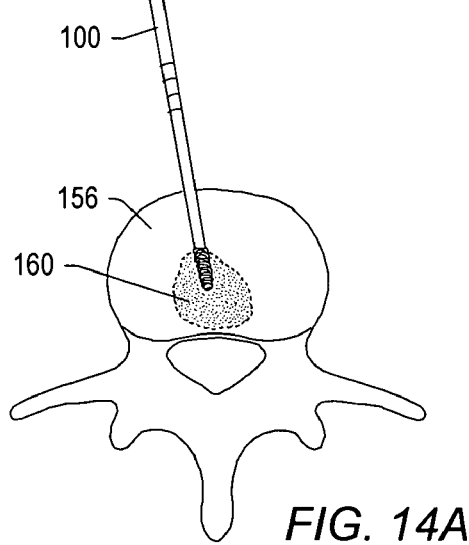
FIG. 14A and FIG. 14B depict insertion of fluid into a bone using an anterolateral approach.
Figure 14B:
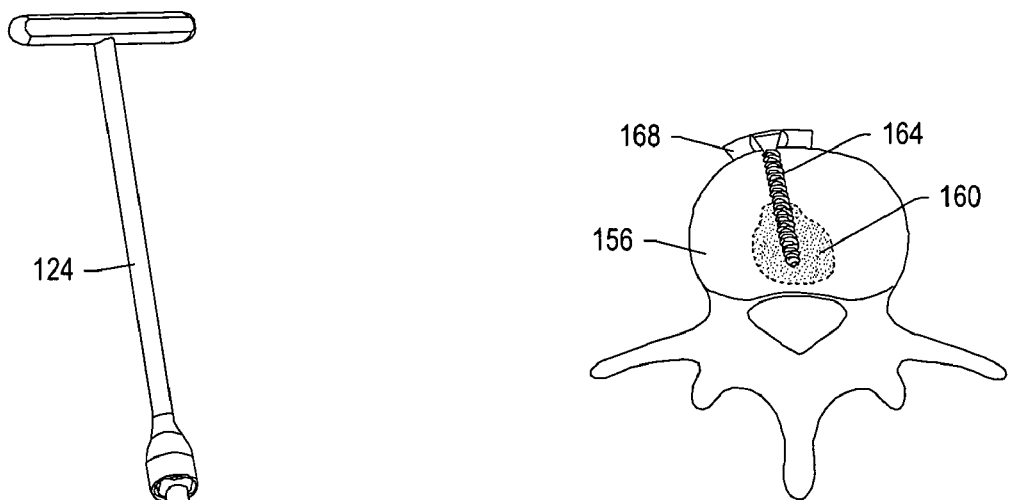

In some stabilization procedures, a fastener may be inserted into a vertebra using an anterolateral approach. FIG. 14A depicts bone tap 100 that was inserted into vertebral body 156 using an anterolateral approach. Bone cement 160 has been introduced through bone tap 100 into vertebral body 156. Driver 124 is positioned on bone tap 100 to facilitate removal of the bone tap from vertebral body 156. After injection of bone cement and removal of bone tap from the vertebral body, a bone plate system or other stabilization system may be coupled to the vertebral body. FIG. 14B depicts bone plate 168 coupled to vertebral body 156 by bone fastener 164. A portion of thread of bone fastener 164 is positioned in bone cement 160 placed in the vertebral body using the bone tap.

In some embodiments, a fenestrated bone tap may be used in a procedure to introduce bone cement into a fractured or diseased bone. In some embodiments, the bone may be a vertebra. For example, vertebroplasty may be used to treat a compression fracture resulting from osteoporosis in a vertebra. The vertebra may include, but is not limited to, a lumbar vertebra or a lower thoracic vertebra. In some embodiments, a fenestrated bone tap may be used to introduce bone cement into a void in a bone created by surgical removal of a tumor. A bone tap used for vertebroplasty may be similar to bone taps depicted in FIGS. 1-6.

Figure 15:
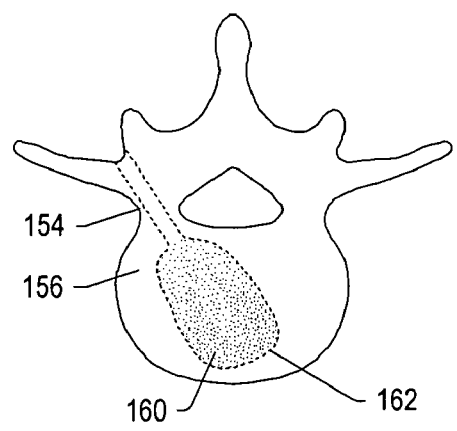
FIG. 15 depicts bone cement insertion after a vertebroplasty procedure performed with a fenestrated bone tap.

Bone cement may be introduced through a bone tap as the bone tap is being withdrawn from a bone to fill the central passage formed by the bone tap and to provide a long stabilization area in the bone. If needed, a wrench coupled to a tool portion (e.g., tool portion 108 depicted in FIG. 1) may be used to facilitate backout of the bone tap so that bone cement may be introduced into a long stabilization area. FIG. 15 depicts bone cement positioned in vertebral body 156 with a fenestrated bone tap.

In some embodiments, one or more bones adjacent to a target bone may be augmented before a target bone is augmented. For example, a vertebroplasty may be performed to correct a fractured L4 vertebra. Before tapping and injecting bone cement into the target L4 vertebra, the surgeon may tap and inject bone cement into the L3 vertebra (immediately superior to the L4 vertebra) and the L5 vertebra (immediately inferior to the L4 vertebra). The bone cement may address weakness in the L3 and L5 vertebrae caused by osteoporosis or other factors. After the bone cement in the L3 and L5 vertebra has partially or fully cured, the surgeon may tap and inject bone cement into the target L4 vertebra. Using bone augmentation to strengthen bones adjacent to a target bone may reduce the risk of a strengthened target bone damaging a softer or weaker adjacent bone. In some embodiments, adjacent bones may be augmented with bone cement during or after augmentation of the target bone. In some embodiments, adjacent portions of a target portion of a single bone (e.g., a femur) may be augmented before, during, or after the target portion is augmented.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of introducing a fluid into a bone, comprising:
preparing an opening in a bone using a bone tap, the bone tap comprising a body, a passage extending along at least a portion of the body, one or more openings located at a distal end of the body and communicating with the passage, and threading located near the distal end of the body of the bone tap;
introducing a fluid to the bone through the passage and at least one of the openings of the bone tap, wherein the fluid comprises bone cement;
allowing the bone cement to spread to a portion of the bone, wherein the bone cement is allowed to harden at least partially before the bone tap is removed from the opening in the bone formed by the bone tap;
removing the bone tap from the opening in the bone; and
introducing a bone fastener into the opening in the bone formed by the bone tap, wherein the portion of the bone filled with the bone cement maintains a shape complementary to the distal end of the body of the bone tap following the removal of the bone tap and prior to the introduction of the bone fastener.

2. The method of claim 1, wherein preparing the opening in the bone using the bone tap further comprises attaching a driver to the bone tap, placing the bone tap at an initial opening formed in the bone, and rotating the driver to thread the bone tap into the bone.

3. The method of claim 1, wherein introducing the fluid to the bone comprises coupling a fluid delivery system to the bone tap, and activating the fluid delivery system to move fluid through the bone tap and into the bone.

4. The method of claim 1, wherein the step of introducing a fluid to the bone comprises the steps of:
(1) introducing the fluid in the opening in the bone formed by the bone tap;
(2) partially withdrawing the bone tap from the opening in the bone formed by the bone tap; and
(3) introducing additional fluid one or more times in the opening in the bone formed by the bone tap.

5. A method of introducing a fluid into a bone, comprising:
preparing an opening in a bone using a bone tap, the bone tap comprising a body, a passage extending along at least a portion of the body, one or more openings located at a distal end of the body and communicating with the passage, and threading located near the distal end of the body of the bone tap;
introducing a fluid to the bone through the passage and at least one of the openings of the bone tap;
allowing the fluid to spread to a portion of the bone wherein the fluid comprises a bone filler and a medicament;
removing the bone tap from the opening in the bone; and
introducing a bone fastener into the opening in the bone formed by the bone tap.

6. The method of claim 5, wherein preparing the opening in the bone using the bone tap further comprises attaching a driver to the bone tap, placing the bone tap at an initial opening formed in the bone, and rotating the driver to thread the bone tap into the bone.

7. The method of claim 5, wherein introducing the fluid to the bone comprises coupling a fluid delivery system to the bone tap, and activating the fluid delivery system to move fluid through the bone tap and into the bone.

8. The method of claim 5, wherein the step of introducing a fluid to the bone comprises the steps of:
(1) introducing the fluid in the opening in the bone formed by the bone tap;
(2) partially withdrawing the bone tap from the opening in the bone formed by the bone tap; and
(3) introducing the fluid again one or more times in the opening in the bone formed by the bone tap.

9. A method of introducing a fluid into a bone, comprising:
preparing an opening in a bone using a bone tap, the bone tap comprising a body, a passage extending along at least a portion of the body, one or more openings communicating with the passage, and threading located near an end of the body of the bone tap;
introducing a fluid to the bone through the passage and at least one of the openings of the bone tap, wherein the fluid comprises bone cement;
allowing the bone cement to spread to a portion of the bone;
coupling a removable driver to the bone tap, and using the driver to remove the bone tap from the opening in the bone, wherein the bone tap is removed from the opening after the bone cement begins to cure; and
introducing a bone fastener into the opening in the bone formed by the bone tap.

10. The method of claim 9, wherein preparing the opening in the bone using the bone tap further comprises attaching a driver to the bone tap, placing the bone tap at an initial opening formed in the bone, and rotating the driver to thread the bone tap into the bone.

11. The method of claim 9, wherein introducing a fluid to the bone comprises coupling a fluid delivery system to the bone tap, and activating the fluid delivery system to move fluid through the bone tap and into the bone.

12. The method of claim 9, wherein the step of introducing a fluid to the bone comprises:
(1) introducing the fluid in the opening in the bone formed by the bone tap;
(2) partially withdrawing the bone tap from the opening in the bone formed by the bone tap; and
(3) introducing additional fluid one or more times in the opening in the bone formed by the bone tap.

13. A method of introducing a fluid into a bone, comprising:
preparing an opening in a bone using a bone tap, the bone tap comprising a body, a passage extending along at least a portion of the body, one or more openings communicating with the passage, and threading located near an end of the body of the bone tap;
introducing a fluid to the bone through the passage and at least one of the openings of the bone tap;
allowing the fluid to spread to a portion of the bone wherein the fluid comprises a bone filler and a medicament;
coupling a removable driver to the bone tap, and using the driver to remove the bone tap from the bone; and
introducing a bone fastener into the opening in the bone formed by the bone tap.

14. A method of introducing a fluid into a bone, said method comprising the steps of:
preparing an opening in a bone using a bone tap, the bone tap comprising:
a body;
a passage through at least a portion of the body;
threading located near a distal end of the body; and
one or more openings through the threading in communication with the passage,
the one or more openings configured to introduce bone filler into the bone;
introducing a fluid to the bone through the passage and the one or more openings in the bone tap;
partially withdrawing the bone tap from the opening in the bone formed by the bone tap;

introducing the fluid again one or more times in the opening in the bone formed by the bone tap, wherein the fluid comprises a bone filler and a medicament; and withdrawing the bone tap from the bone.

15. The method of claim 14, wherein preparing the opening in the bone comprises attaching a driver to the bone tap, placing the bone tap at an initial opening formed in the bone, and rotating the driver to thread the bone tap into the bone.

16. The method of claim 14, wherein introducing the fluid to the bone further comprises coupling a fluid delivery system to the bone tap, and activating the fluid delivery system to move the fluid through the bone tap and into the bone.

17. A method of introducing a fluid into a bone, comprising:

preparing an opening in a bone using a bone tap, the bone tap comprising:
a body;
a passage through at least a portion of the body;
threading located near a distal end of the body; and
one or more openings through the threading in communication with the passage,
the one or more openings configured to introduce bone filler into the bone;

introducing a fluid to the bone through the passage and the one or more openings in the bone tap, wherein the fluid comprises bone cement;

partially withdrawing the bone tap from the opening in the bone formed by the bone tap;

introducing additional bone cement one or more times in the opening in the bone formed by the bone tap; and withdrawing the bone tap from the bone, wherein the bone tap is removed from the opening after the bone cement begins to cure.

* * * * *